United States Patent [19]

Wedding

[11] Patent Number: 5,317,930
[45] Date of Patent: Jun. 7, 1994

[54] CONSTANT FLOWRATE CONTROLLER FOR AN AEROSOL SAMPLER USING A FILTER

[75] Inventor: James B. Wedding, Fort Collins, Colo.

[73] Assignee: Wedding & Associates, Inc., Fort Collins, Colo.

[21] Appl. No.: 762,319

[22] Filed: Sep. 18, 1991

[51] Int. Cl.$^5$ ............................................. G01N 1/24
[52] U.S. Cl. .............................. 73/863.03; 73/863.23
[58] Field of Search ........... 73/863.03, 863.23–863.25, 73/864.34, 864.35

[56] References Cited

U.S. PATENT DOCUMENTS

| | | | |
|---|---|---|---|
| 1,850,030 | 3/1932 | Pardoe | 73/213 |
| 3,699,814 | 10/1972 | Kaufman | 73/864.34 X |
| 3,754,868 | 8/1973 | Witz et al. | 73/863.24 X |
| 3,817,100 | 6/1974 | Anderson et al. | 73/213 |
| 3,862,576 | 1/1975 | Pogorski | 73/863.23 X |
| 3,981,283 | 9/1976 | Kaufman | 123/119 |
| 4,067,705 | 1/1978 | Kurz | 55/278 |
| 4,178,794 | 12/1979 | Jugle et al. | 73/863.25 |
| 4,205,550 | 6/1980 | Swanson | 73/863.24 X |
| 4,246,788 | 1/1981 | Olin et al. | 73/863.23 X |
| 4,461,183 | 7/1984 | Wedding | 73/863.21 |
| 4,649,760 | 3/1987 | Wedding | 73/863.23 |
| 4,677,863 | 7/1987 | Gay et al. | 73/863.23 X |
| 4,961,916 | 10/1990 | Lesage et al. | 73/862.23 X |
| 4,974,455 | 12/1990 | McGowon et al. | 73/863.23 X |
| 5,010,776 | 4/1991 | Lucero et al. | 73/862.23 |
| 5,054,328 | 10/1991 | Long et al. | 73/864.81 |
| 5,076,097 | 12/1991 | Zarrin et al. | 73/61.72 |

FOREIGN PATENT DOCUMENTS 1494111 7/1967 France .

OTHER PUBLICATIONS

Durgin, William W., editor "Flow, Its Measurement and Control in Science and Industry," vol. Two, 1981, St. Louis, pp. 431–439; A Relation Between Sonic Venturi Profile and its Unchoking Back-Pressure Ratio; K. Komiya et al.

Shapiro, Ascher H., "The Dynamics and Thermodynamics of Compressible Fluid Flow," vol. One, New York, pp. 140–142.

Primary Examiner—Tom Noland
Attorney, Agent, or Firm—James R. Young

[57] ABSTRACT

A constant flow rate controller apparatus for an aerosol sampler using a filter includes an enclosed channel for channeling a stream of air, a filter positioned in the channel to capture and retain particles while allowing the stream of air to flow therethrough, an air or vacuum pump to pull the air through the filter, and a flow controller that maintains a constant volumetric flow rate of air through the sampler and filter, regardless of how much particulate matter is deposited on the filter or how much pressure drop across the filter changes due to particulate loading. The filter can be a substantially non-fibrous, porous, this film membrane medium, for which the flow controller of this invention is particularly beneficial, or it can be a more conventional fibrous medium. The flow controller can include a critical or choked flow orifice with a variable effective flow area, which effective flow area can be varied in response to changes in pressure drop across the filter to maintain constant volumetric flow rate. An expandable and contractible bellows with an appropriate spring constant can be used to both sense changes in air pressure drop across the filter or changes in stagnation pressure downstream of the filter and to actuate a variation in the effective flow area of the orifice in response to such changes in air pressure to maintain constant volumetric flow rate of the air. The air or vacuum pump has to have enough capacity to maintain critical or choked flow conditions in the orifice.

46 Claims, 4 Drawing Sheets

CONSTANT FLOWRATE CONTROLLER FOR AN AEROSOL SAMPLER USING A FILTER

BACKGROUND OF THE INVENTION

1. Field of the Invention

The present invention relates generally to aerosol sampling methods and devices for sampling particulate matter in ambient air, and more specifically to a flow rate control method and apparatus for use with a filter.

2. Description of the Prior Art

It is now generally recognized and accepted that particulate matter in air, especially particles smaller than 10 micrometers in diameter, which can be inhaled easily and deposited in the tracheo-bronchial regions of the human respiratory tract, pose substantial health concerns. Consequently, the United States Environmental Protection Agency (EPA) has established a National Ambient Air Quality Standard in 52 Fed. Reg. 24634–24735, 40 CFR Part 50, which strictly limits amounts of particulate matter of less than 10 micrometer size in ambient air, since the principal target is the human lung, a long term integrating receptor. This National Ambient Air Quality Standard is expressed in terms of maximum allowable ambient concentrations of particles having aerodynamic diameters smaller than a nominal 10 micrometers ($PM_{10}$) for both annual and daily time periods.

Accurate, precise and reliable monitoring equipment is required to demonstrate compliance or noncompliance with the EPA Ambient Air Quality Standard. Such monitoring equipment needs to be able to take in samples of particle-laden ambient air in a consistent, representative manner over the specified sample or test time period, separate the particles smaller than 10 micrometers ($PM_{10}$) from the larger particles, and collect the $PM_{10}$ particles for measuring, weighing, or other analyses. My U.S. Pat. No. 4,461,183 illustrates an aerosol sampler inlet that meets the EPA specifications for collecting ambient particle samples and separating $PM_{10}$ particles from larger particles in the sample for passing on to an appropriate $PM_{10}$ particle collector, which has been specified by EPA in 40 CFR Part 50 to be a filter medium having a specific efficiency for test particles and certain physical and chemical properties. It was also determined, however, that the accuracy of such sampler inlets requires specific and constant air velocities throughout the sampling time period, regardless of varying ambient conditions of wind velocities and directions, air temperatures, and quantities of $PM_{10}$ particulate matter trapped in or on the filter medium. Consequently, the EPA rule in 40 CFR Part 50, Appendix J, requires that ". . . specific air velocities be maintained in the sampler's air inlet system." 52 Fed. Reg. 24665. Therefore, the volumetric flow rate through the sampler's inlet must be maintained constant, within inlet design tolerances, throughout the sampling period. The flow controller method and apparatus disclosed in my U.S. Pat. No. 4,649,760 utilizes a critical (choked) flow venturi to achieve such constant volumetric flow rate control for accurate aerosol sampling and monitoring, as required by the EPA regulations.

While a 24-hour mean concentration of $PM_{10}$ is a useful measure of particle concentration as it affects health, as described above, it is less useful for identifying specific diurnal patterns in mass concentration of the particles or for identifying emission sources of specific particles within the standard 24-hour sampling periods. Consequently, even more sophisticated sampling is required to identify given species or elements of particles captured in the ambient aerosol samples, rather than just the total mass of $PM_{10}$ particles deposited onto the sampler's filter medium in a 24-hour period. More sophisticated aerosol sampling is also required to identify sources of such air-borne particles, for example, by collecting and recording more sampling periods and perhaps in sampling periods of shorter duration, such as every hour.

Unfortunately, the fibrous glass or quartz filter media customarily used in monitoring total $PM_{10}$ mass collected over a 24-hour period cannot be used effectively for numerous, shorter sample periods where it is desired to identify and quantify given particulate or elemental species collected from the ambient air during each period. Such filters are quite friable an tend to lose portions of the edge fibers during handling, requiring a large filter to minimize the impact of these losses. This in turn requires a long sampling time to collect enough particulate matter. In addition, such filters are rather soluble, and thus interfere with many analytical measurements, and many of them also contain variable amounts of the elements it is desired to measure. Their structure also does not permit microscopy of the collected samples.

Numerous other filter types are available, including membrane filters (non-fibrous filters with variously formed pores of typical mean diameters from about 0.1 to about 10 micrometers), fabricated from a variety of polymeric materials from cellulose esters to PTFE ("Teflon" trademark), and including PVC (polyvinyl chloride) and polycarbonate ("Lexan" trademark). Each of these filter materials is a filter of choice for some purposes in the measurement of atmospheric pollution. Each of them has different characteristics of flow rate versus pressure drop, and all of them have markedly higher pressure drops at any given flow rate than fibrous glass or quartz filter media. These pressure drops for such membrane filter media are sufficiently high that neither the flow controller nor the air mover of my method and apparatus for controlling flow volume through an aerosol sampler described in my U.S. Pat. No. 4,649,760 can function as required using any practical filter size. Also, as shown by the U.S. Pat. No. 4,961,916, issued to J. Lesage, et al., there are also specific types of filters with special chemical impregnation for sampling toxic vapors, which also have different and varying flow rate to pressure drop characteristics.

At the present time, at least prior to this invention, there were no samplers available that could collect $PM_{10}$ particulate matter or other airborne liquid or solid matter using the same sampler on a variety of filter substrates while maintaining constant volumetric flow rate of the air flowing through the sampler for the duration of the desired or needed sampling periods, as required by 40 CFR Part 50, Appendix J, or as required by the sampler inlet design specifications for maintaining accurate $PM_{10}$ particle separation or other criteria..

SUMMARY OF THE INVENTION

Accordingly, it is general object of the present invention to provide an aerosol sampler that can collect particulate mass or other airborne liquid or solid matter from ambient air in a manner that provides the means for subsequent elemental analysis of collected particulate matter on the filter medium or for other purposes, while also maintaining constant volumetric air flow rate through the sampler inlet as required to meet the desired particle size and effectiveness cut point specifications.

It is another object of this invention to provide a method and apparatus for collecting particulate matter from an ambient air sample in manner that meets the needs of a variety of air pollution studies after the air sample passes through a fractionator inlet that retains larger particles and passes particles of the desired size range, wherein the effectiveness and efficiency of the inlet operation requires a constant design volumetric flow rate of air therethrough.

A more specific object of the present invention is to provide a method and apparatus for maintaining a constant design volumetric flow rate of air through a sampler inlet and particle-catching filter medium wherein particles collecting on the filter medium substantially impede the flow of air therethrough.

Another specific object of this invention is to provide a sampling system that can utilize a wide variety of filter media and still maintain a constant, known and theoretically predictable sampling flow rate without needing recalibration or other adjustment.

Additional objects, advantages, and novel features of the invention will be set forth in part in the description that follows and in part will become apparent to those skilled in the art upon examination of the following or may be learned by the practice of the invention. The objects and advantages of the invention may be realized and obtained by means of the instrumentalities and in combinations particularly pointed out in the appended claims.

To achieve the foregoing and other objects and in accordance with the purpose of the present invention, the constant flow rate controller apparatus for an aerosol sampler using a filter includes an enclosed channel for channeling a stream of air, a filter positioned in the channel to capture and retain particles while allowing the stream of air to flow therethrough, an air or vacuum pump to pull the air through the filter, and a flow controller that maintains a constant volumetric flow rate of air through the sampler and filter, regardless of how much particulate matter is deposited on the filter or how much pressure drop across the filter changes due to particulate loading. The filter can be a substantially non-fibrous, porous, thin film membrane medium, for which the flow controller of this invention is particularly beneficial, or it can be a more conventional fibrous medium. The flow controller can include a critical or choked flow orifice with a variable effective flow area, which effective flow area can be varied in response to changes in pressure drop across the filter to maintain constant volumetric flow rate. An expandable and contractible bellows with an appropriate spring constant can be used to both sense changes in air pressure drop across the filter or changes in stagnation pressure downstream of the filter and to actuate a variation in the effective flow area of the orifice in response to such changes in air pressure to maintain constant volumetric flow rate of the air. The air or vacuum pump has to have enough capacity to maintain critical or choked flow conditions in the orifice.

The method of sampling particles according to this invention includes drawing particle-laden air through a filter medium that can be either fibrous or a porous, non-fibrous, thin film membrane or other filter type, and maintaining constant volumetric flow rate of air through the filter, regardless of substantial changes in pressure drop across the filter due to particles retained on the filter. Controlling the flow rate to achieve constant volumetric flow rate according to this invention can include passing the air through a critical flow orifice that has a variable effective flow area, pumping a sufficient flow of air to maintain critical or choked flow condition in the orifice, sensing changes in pressure drop across the filter or changes in stagnation pressure downstream of the filter, and varying the effective flow area of the orifice to compensate for the changes in pressure in a manner that maintains constant volumetric flow rate therethrough.

Additional details of both the apparatus and method of this invention will be described below.

BRIEF DESCRIPTION OF THE DRAWINGS

The invention, together with further objects and advantages thereof, may be best understood by reference to the following description taken in conjunction with the accompanying drawings and in which.

DETAILED DESCRIPTION OF THE PREFERRED EMBODIMENTS

Figure 1:
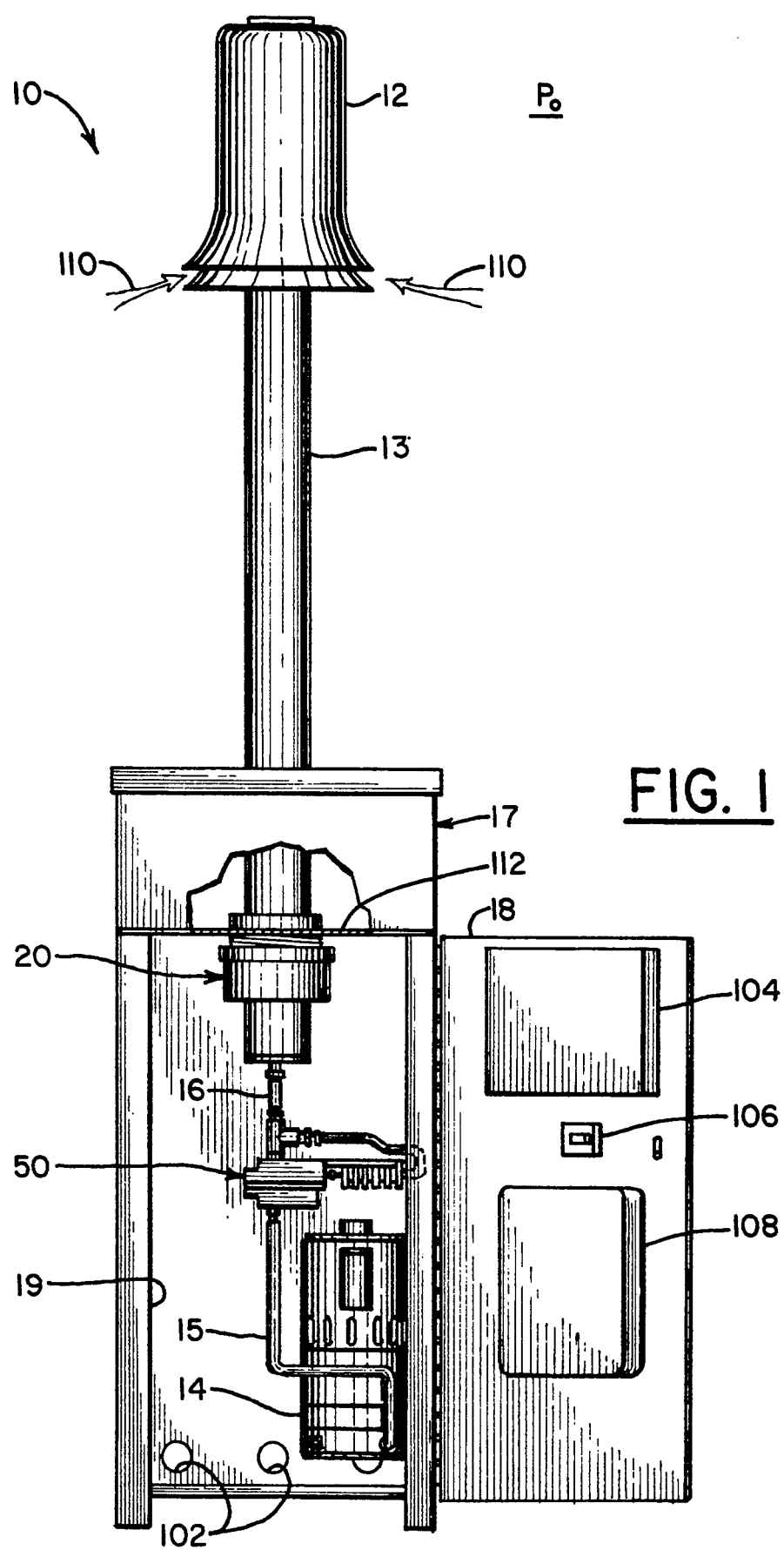
FIG. 1 is an elevation view of the front of an aerosol sampler with its access door opened and a portion of its front panel cut away to reveal the filter assembly and flow controller of the present invention.

An ambient aerosol sampler 10 equipped with a filter assembly 20 and an air flow controller 50 according to the present invention is generally illustrated in FIG. 1 and will be described in more detail by reference to FIGS. 2-5. It is illustrated with an aerosol inlet 12 for drawing aerosol samples into the sampler 10 and for separating larger aerosol particles in the sample from smaller ones, although the inlet 12 is not a part of this invention. It also has a filter assembly 20 connected to the inlet 12 by a duct 13, a flow controller 50 for maintaining a constant volumetric flow rate of air through the inlet 12 and the filter assembly 20, and a vacuum pump 14 connected by conduits 15 and 16 to the flow controller 50 and filter assembly 20 for drawing the aerosol sample through the sampler 10, as will be described in more detail in subsequent paragraphs.

The filter assembly 20, flow controller 50, and vacuum pump 14 are mounted in a cabinet 17, which has an access door 18 for closing an access opening 19. Outlet holes 102 are provided in the walls of the cabinet 17 to allow exhaust air to be discharged. Additional equipment, such as a timer 104, an elapsed time indicator 106, and a pressure recorder 108, which are useful in using the aerosol sampler, are shown mounted on the inside surface of the access door 18.

As mentioned above, the vacuum pump 14 pulls ambient air into the sampler inlet 12, as indicated by the arrows 110, when such an inlet is used along with the apparatus of the invention. The inlet 12, when used, will preferably, although not necessarily, be a fractionating inlet of the type described in my U.S. Pat. No. 4,461,183, issued on Jul. 24, 1984, which is incorporated herein by reference. As described therein, when the air flow is maintained at a constant design volumetric flow rate through the inlet 12, such as 4 c.f.m. (cubic feet per minute), the inlet separates aerosol particles having aerodynamic diameters of 10 micrometers and above and retains them while allowing particles of less than 10 micrometers ($PM_{10}$) to pass therethrough with a separation efficiency that meets the EPA criteria for such equipment.

The air stream carrying the $PM_{10}$ particles then passes through duct 13 to the filter assembly 20. When no particular inlet is used, the air stream can be drawn directly into the filter assembly 13, preferably, although not necessarily, through some kind of duct or air channel. The filter assembly 20 intercepts and retains the $PM_{10}$ or other particles in the sample air stream throughout the sample period for subsequent removal, weighing, and other analyses. The flow controller 50 maintains the air flowing through the inlet 12 and through the filter assembly 20 at a constant volumetric flow rate, regardless of ambient temperature and filter loading, as will be described in more detail below. The constant volumetric flow rate maintained by the flow controller assembly 50 is preferably the design flow rate for which the inlet 12 is designed to operate, as described above, although any desired flow rate can be maintained according to this invention.

Figure 2:
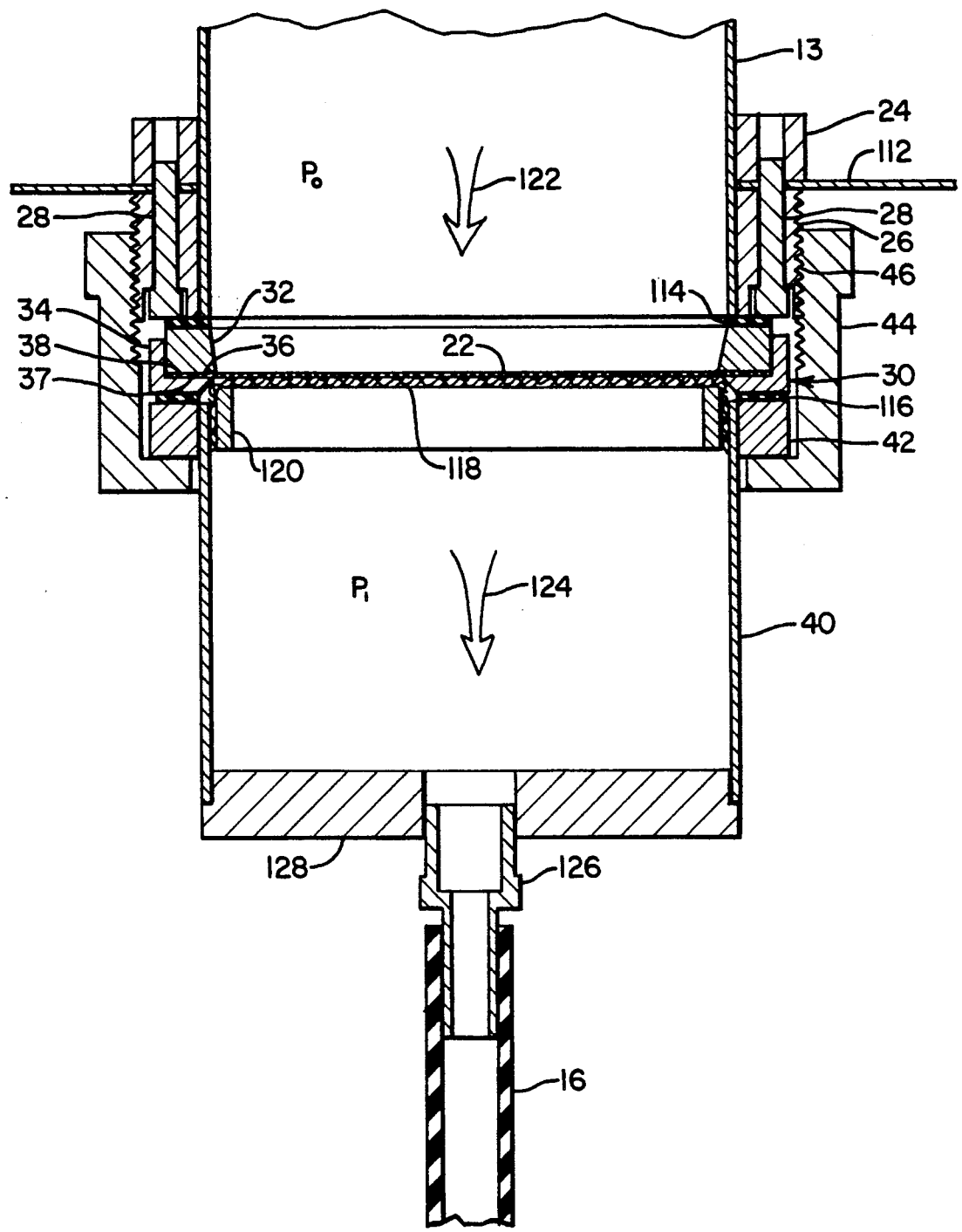
FIG. 2 is an enlarged cross-sectional view of the filter assembly of the present invention.

The filter assembly 20, as best seen in FIG. 2, includes a porous filter 22 positioned across the air flow path coming through the duct 13 from the sampler inlet 12 (not shown in FIG. 2). The lower end of the duct 13 is anchored to a partition panel 112 of the cabinet 17 (not shown in FIG. 3) by an annular collar comprising an upper ring 24 positioned over partition 112 and a lower ring 26 positioned below partition 112 and clamped together by bolts 28.

The filter medium 22 is retained in position by an annular filter cassette 30 comprising an inner ring 32 and an outer ring 34. The peripheral edge 36 of the filter 22 is compressed between mating surfaces 37, 38 of the inner ring 32 and outer ring 34, respectively. A cylindrical chamber 40 and an annular shoulder 42 around its upper end abut the outer ring 34 of filter cassette 30, and, when forced by a retainer nut 44 screwed onto the threaded peripheral surface 46 of the lower ring 26, compresses the inner ring 32 against the outer ring 34. An upper gasket 114 positioned between inner ring 32 of cassette 30 and lower ring 26 and a lower gasket 116 positioned between the outer ring 34 of cassette 30 and the shoulder 42 seal the air stream inside the filter assembly 20 from the air outside. A screen backing 118 for supporting the filter 22 is retained in position at the top of chamber 40 by an annular retainer ring 120.

As the air sample flows out of duct 13, as indicated by arrow 122 in FIG. 2, and through the filter medium 22, the filter medium 22 retains essentially all of the $PM_{10}$ particles transmitted through the inlet 1 (not shown in FIG. 2) or other particles if an inlet 12 is not used. The air stream then continues sans particles through the chamber 40, as indicated by arrow 124, and into connecting tube 16, which leads to the flow controller apparatus 50 (not shown in FIG. 2). The connecting tube 16 is connected to chamber 40 by a fitting 126 screwed into the bottom end wall 128 of chamber 40.

After a sample is collected for the desired or prescribed period of time, the filter medium 22 can be removed quite easily to weigh and/or analyze the $PM_{10}$ or other particles deposited thereon. Essentially, the retainer nut 44 can be unscrewed from the lower ring 26, so the chamber 40 can be lowered away from the bottom of duct 13. By making the connecting tube 16 a length of flexible tube, this removal process can be facilitated. The filter cassette 30 can then be removed, and the outer ring 34 can be separated from the inner ring 32 to release the filter medium 22. A new filter medium 22 can be installed quite easily and quickly by reversing the filter removal process described above.

While the filter medium 22 can be a fibrous material, such as those used in prior art aerosol samplers, there are some substantial advantages in using a non-fibrous filter membrane, such as "Gore-Tex" (trademark) expanded PTFE (polytetrafluoroethylene) laminate films, manufactured by W. L. Gore & Associates, Inc., of Elkton, Md., best known by the DuPont trademark "Teflon," or other non-fibrous media such as "Nuclepore" (trademark) manufactured by Costar-Nuclepore Corporation, of Pleasanton, Calif., "Versapore" (trademark) manufactured by Gelman Sciences, of Ann Arbor, Mich., and "Nylasorb" (trademark) also manufactured by Gelman Sciences, of Ann Arbor, Mich.

Such non-fibrous filter media should be sufficiently porous to allow passage of air therethrough, but the pores should also be small enough to not pass any of the $PM_{10}$ fraction particulates. Pore sizes in the range of 0.1 micrometer to 5.0 micrometers are satisfactory for the purposes described for this invention. Unfortunately, such non-fibrous, thin, porous filter membranes as described above tend to have high initial flow resistance and to have the pores plugged much more quickly by particles retained thereon than the thicker, higher porosity fibrous filter media used in the prior art. As a result, the resistance to air flow through the filter membrane 22 can increase rapidly as the $PM_{10}$ fraction or other particles are retained thereon, and the pressure drop across such filter membrane 22 increases accordingly. Consequently, prior art flow controllers, such as the critical flow venturi described in my U.S. Pat. No. 4,649,760, issued on Mar. 17, 1987, which work so well with the EPA-prescribed fibrous filter medium, are not effective to maintain a constant volumetric flow rate through such thin membrane filter media.

The flow controller apparatus 50 of this invention, on the other hand, is designed especially for maintaining a constant volumetric flow through a rapidly loading filter medium, such as the PTFE or other non-fibrous filter membranes described above, thus also maintaining the required constant volumetric flow rate through the sampler inlet 1 for efficient and effective particle fractionation that meets the EPA rules for such devices. As mentioned above, the collection of accurate and meaningful $PM_{10}$ concentrations is intimately related to proper flow control of the aerosol sample through the sampler 10. First, calculation of mass concentration $M_c$ requires an accurate and proper volumetric flow rate, according to the formula:

$$M_c = \frac{\text{Collected Mass}}{Q \cdot \Delta t} \qquad (1)$$

where Q is the volumetric flow rate and $\Delta t$ is elapsed sampling time. Specifically, the denominator for the calculation of mass concentration $M_c$ requires an accurate flow rate Q, the numerator being the collected mass of the $PM_{10}$ on the filter medium 22 during the sample period. Second, as mentioned above, the inlet 12, when used, requires a constant volumetric flow rate within the design parameters of the inlet 12 to achieve the proper PM$_{10}$ particle fractionation from the aerosol sample collected. Failure to maintain required material velocities or volumetric flow rates would preclude the accurate and precise measurement of dosage indication of particles to the thoracic region of the human respiratory system. Further, it is an EPA requirement that the flow control device maintain constant design flow rate conditions at ambient or site conditions of temperature and pressure. When the further parameter of the decreasing stagnation pressure downstream of the filter 22 due to filter loading is encountered, as described above, an accurate and effective flow controller, such as the flow controller 50, is an essential element of the sampler 10 according to this invention.

It was shown in my U.S. Pat. No. 4,649,760, issued on Mar. 17, 1987, which is incorporated herein by reference, that a critical flow device can provide an accurate flow rate measurement and control for an aerosol sampler, albeit that device is limited to applications where pressure drop across the filter is low and does not change significantly during the sampling period. Volumetric flow rate measurement with a critical flow device flow controller can be calculated according to the following formula:

$$Q = C_f A_s \left[ C \left( \frac{R}{M_w} \right)^{\frac{1}{2}} \right] \left( \frac{P_1}{P_0} \right) \cdot (T_0)^{\frac{1}{2}} \quad (2)$$

where:
Q = Volumetric Flow Rate
$C_f$ = Flow Coefficient
$A_s$ = Critical Flow Device Slot Area
C = Constant
R = Universal Gas Constant
$M_w$ = Molecular Weight of Air
$P_1$ = Stagnation Pressure, Downstream of Filter
$P_0$ = Ambient Pressure
$T_0$ = Ambient Temperature However, in my U.S. Pat. No. 4,649,760, as mentioned above, a fibrous filter medium was used in the aerosol sampler to collect the PM$_{10}$ particulate matter, and such thicker, fibrous filters, when loaded with particles, do not impede the flow of air therethrough significantly. Consequently, the stagnation pressure P$_1$ downstream of the filter in such prior art device remained essentially unchanged, or at least changed only in conjunction with the ambient atmospheric pressure P$_0$. Consequently, the P$_1$/P$_0$ factor in the formula (2) above remained essentially unchanged. Therefore, measurement and calculation of volumetric flow rate Q$_0$ remained substantially unchanged, as long as the choked flow condition in the venturi was maintained.

On the other hand, when using a non-fibrous, thin film porous filter membrane 22 instead of a fibrous filter medium, as described above, the pores plug more quickly, thus restricting air flow through the filter 22 and causing stagnation pressure P$_1$ downstream of the filter medium to drop very significantly during the aerosol sampling period. Consequently, according to formula (2) above, substantial change in pressure drop across the filter medium 22 would cause a substantial change in volumetric flow rate Q of air through the sampler 22 during the sample period, if a prior art critical flow venturi flow controller, such as that described in my U.S. Pat. No. 4,649,760 was used, which would be unacceptable for meeting any of the criteria or standards discussed above for monitoring or measuring aerosol in the air.

Figure 3:
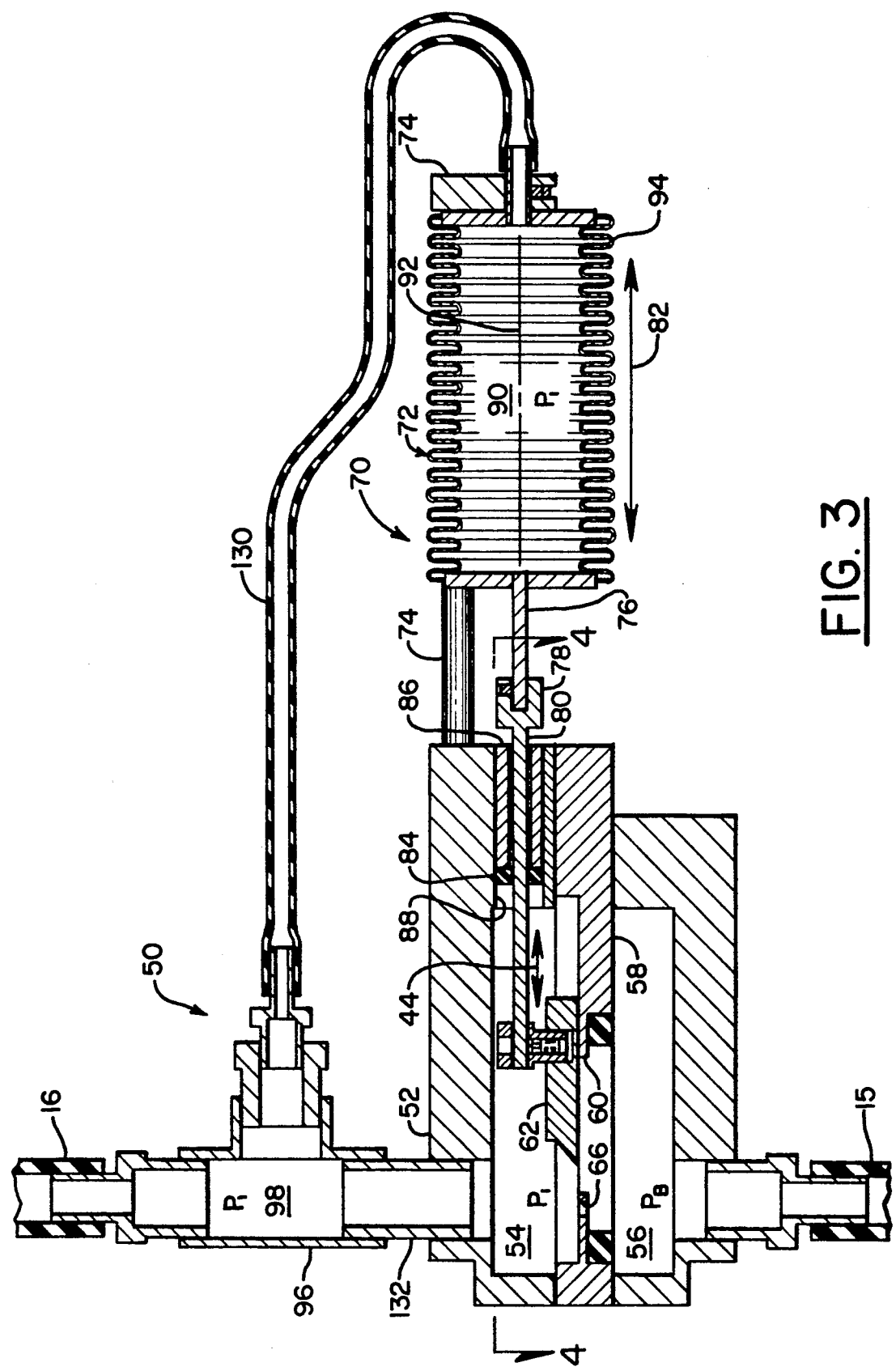
FIG. 3 is an enlarged cross-sectional view of the flow controller assembly according to the present invention.

The flow controller apparatus 50, according to this invention, is provided to maintain constant volumetric flow rate Q automatically throughout an aerosol sampling period, regardless of filter loading, change in pressure drop across the filter membrane 22, or change in stagnation pressure P$_1$ downstream of the filter membrane 22. Referring now to FIGS. 1 and 3, the flow controller apparatus 50 of the present invention is positioned in the air stream, preferably, but not necessarily, downstream of the filter assembly 20. It is connected to the chamber 40 (FIG. 2) of filter assembly 20 by the connecting tube 16 and to the vacuum pump 14 by the vacuum conduit 15.

Figure 4:
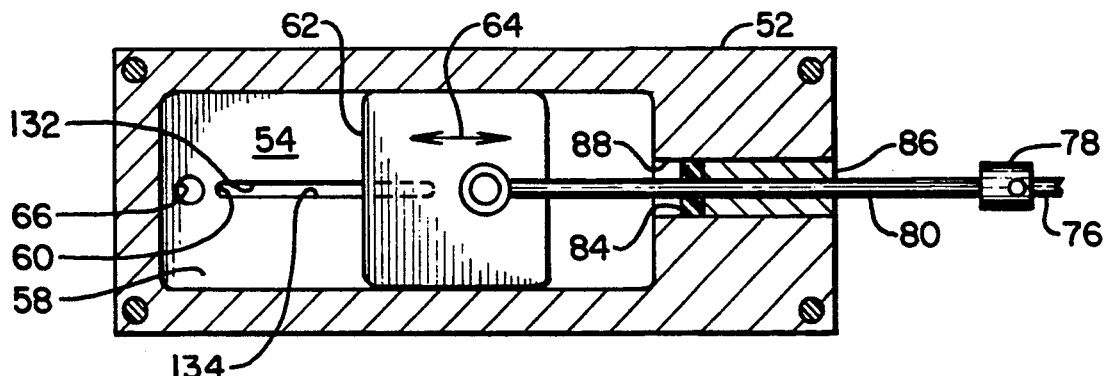
FIG. 4 is a cross-sectional view of the flow controller orifice and slide taken along lines 4—4 of FIG. 3.
Figure 5:
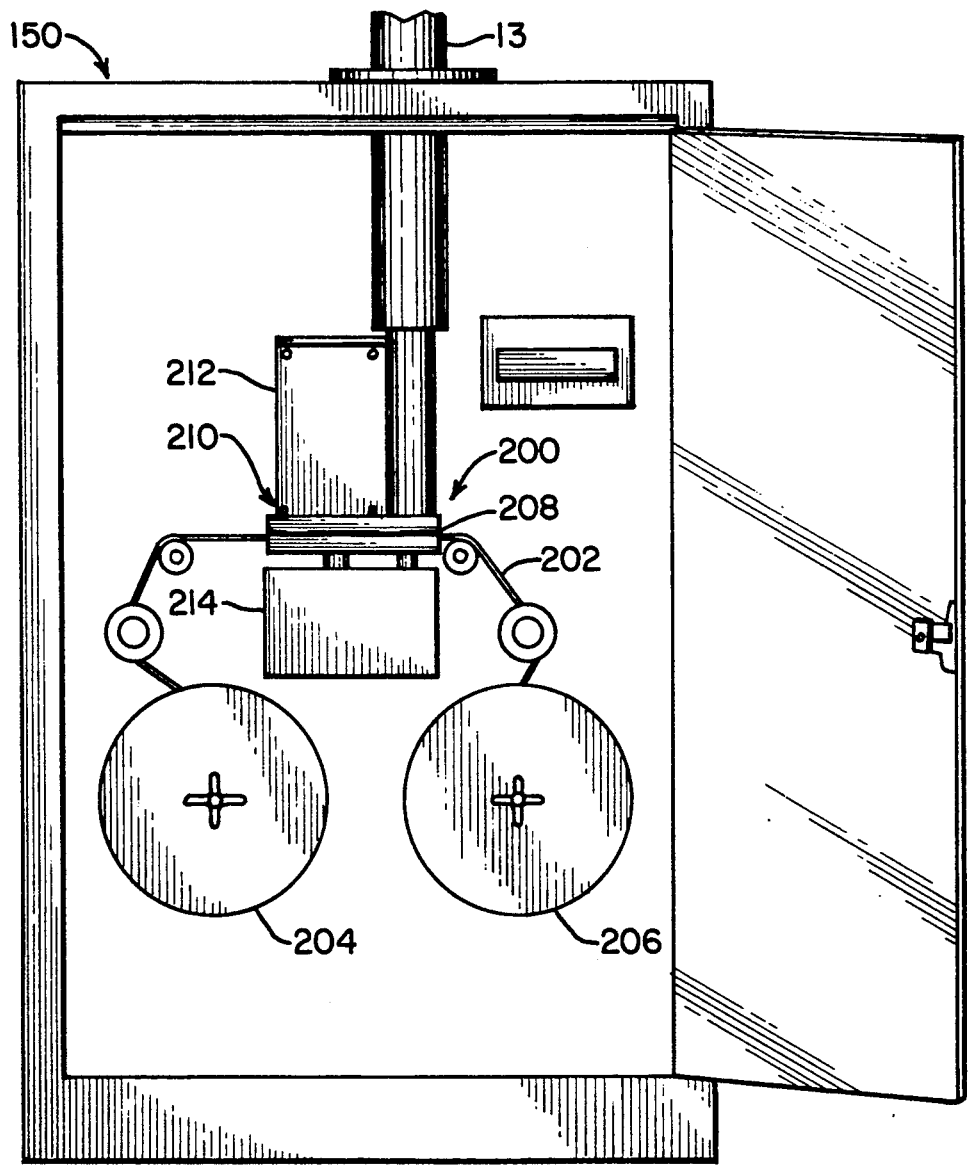
FIG. 5 is a front elevation view of an alternate embodiment filter and analyzer assembly according to the present invention.

The flow controller 50 comprises a housing 52 that contains an upper chamber 54 and a lower chamber 56 separated by a partition 58. The partition 58 has a orifice 60 extending therethrough and connecting the upper chamber 54 in fluid-flow relation to the lower chamber 56. A moveable gate or slide 62 is positioned over the orifice 60 for varying the effective size or cross-sectional area (also sometimes referred to as the effective flow area) of the orifice 60. As best seen in FIG. 4, the orifice 60 is preferably, but not necessarily, in the shape of a narrow, elongated slot. As the slide 62 moves back and forth in upper chamber 54, as indicated by arrow 64, it effectively opens and closes more or less of the orifice 60, thus varying the effective open or flow area of the orifice 60, for a purpose that will be described below. In addition to the slotted orifice 60, a bypass orifice 66 can also provided through partition 58 to provide additional accuracy and precision in higher flow rate applications.

An actuator mechanism 70 for moving the slide 62 back and forth over slotted orifice 60 is best seen in FIG. 3. It may comprise an expandable and contractible bellows 72 mounted on a support bracket 74 that extends outwardly from housing 52. A bellows rod 76 is connected by coupling 78 to a gate rod or slide rod 80, which is engaged with the slide 62. Therefore, as the bellows expands and contracts axially, as indicated by arrow 82, the rods 76, 80 move the slide 62 back and forth, as indicated by arrow 44. The slide rod 80 extends from the upper chamber 54 through a rod bore 88 in housing 52 to the exterior of the housing 52. An annular seal or packing 84 retained by a suitable gland 86 in rod bore 88 seals the upper chamber 54 from the outside, thus preventing pressure or vacuum leakage, while allowing the slide rod 80 to slide in and out, as described above.

The expandable and contractible cylindrical sidewall 94 of bellows 72 encloses a bellows chamber 90, which, when exposed to a higher pressure, causes the bellows to expand in the direction of its longitudinal axis 92, and when the pressure in chamber 90 is decreased, the bellows contracts axially, as indicated by the arrow 82. The sidewall 94 of the bellows 72 is preferably fabricated of a flexible and resilient material such that it functions like a spring with an appropriate spring constant. Therefore, changes in pressure in chamber 90 cause axial movement of bellows rod 76, thus movement of slide 62.

A T-fitting 96 with an interior chamber 98 is positioned in the air flow stream between the connecting tube 16 from filter assembly 20 (FIG. 2) and the upper chamber 54 in housing 52 for connecting the bellows chamber 90 via tube 130 to the air pressure in the system downstream from the filter 22. The T-fitting 96 is shown in FIG. 3, connected to housing 52 via a connecting tube 132. The purpose of this configuration, as will be described in more detail below, is to provide the stagnation pressure $P_1$ downstream of the filter 22 to the bellows chamber 90. Ideally, the pressures in the filter chamber 40, T-fitting housing 98, bellows chamber 90, and upper chamber 54 in housing 52 should all be the same and should be the stagnation pressure $P_1$. Air flow dynamics, friction, restrictions, and the like through the various tubes and fittings could cause pressures to vary somewhat from this ideal, but not significantly. If such variation is significant, it might be desirable to provide larger connections and tubes, and it might also be desirable to connect tube 130 directly to the filter chamber 40 (not shown) to achieve a more accurate measurement of $P_1$ by a direct connection between bellows chamber 90 and the stagnation pressure $P_1$ in filter chamber 40.

As mentioned above, the lower chamber 56 of housing 52 is connected via vacuum conduit 15 to vacuum pump 14 (FIG. 1). The vacuum pump 14 should have sufficient capacity not only to pull the required volume of air through the sampler inlet 12 to meet its design requirements, as described above, but also to maintain a critical or "choked" sonic velocity flow in the slotted orifice 60 and in the bypass orifice 66 (if a bypass orifice is used) in flow controller 50, regardless of decreased stagnation pressure $P_1$ downstream of the filter 22 due to particulate loading on filter medium 22, as will be described in more detail below.

As the aerosol sampler 10 is operating, according to this invention, particle laden air is drawn into the inlet 12, as shown by the arrows 110 in FIG. 1. Fractionation takes place in the inlet 12, which transmits the $PM_{10}$ particle fraction of the aerosol sample. As mentioned above, this particle fractionation in inlet 12 only occurs properly when the volumetric flow rate of air through the inlet is maintained at the design flow rate. The $PM_{10}$ particle laden air stream then continues through a closed air channel comprising the duct 13, filter assembly 20, connecting tube 16, flow controller 50, and vacuum tube 15 to the vacuum or air pump 14. The duct 13 conducts the air stream to the filter assembly 20, where the air passes through the filter medium 22 (FIG. 2), and the remaining $PM_{10}$ particle fraction of the aerosol in the air stream is captured and retained or deposited on the filter medium 22, as described above. As also described above, the stagnation pressure $P_1$ in filter chamber 40, which is the ambient pressure $P_0$ above the filter 22 minus the pressure drop $\Delta P_f$ across the filter 22 ($P_1 = P_0 - \Delta P_f$), decreases as the filter 22 becomes loaded with particulate mass deposited thereon.

From the filter chamber 40, the air stream continues to flow in the air channel through connecting tube 16 to the flow controller 50 (FIG. 3). The air enters the upper chamber 54 in housing 52 of flow controller 50 after having passed through the chamber 98 in T-fitting 96. The air then flows from upper chamber 54 through bypass orifice 66 (if a bypass orifice is used) and through the non-occluded portion of slotted orifice 60 into lower chamber 56, from where it continues through vacuum conduit 15 to the vacuum pump 14, where it is exhausted into the atmosphere. The back pressure $P_B$ in the lower chamber 56 is maintained by the vacuum pump 14.

It is significant to note that where the vacuum pump holds a vacuum or back pressure $P_B$ low enough so that the ratio of back pressure $P_B$ to the stagnation pressure $P_1$ is equal to or less than 0.53, i.e., where $P_B/P_1 \leq 0.53$, air velocity through both orifices 60, 66 will be equal to the velocity of sound (sonic velocity). At these conditions, both the bypass orifice 66 if present and the slotted orifice 60 are in the "choked" or "critical flow" condition, wherein the flow rate of air through the orifices 60, 66 cannot increase any higher. Both orifices 60, 66 will remain choked independent of stagnation pressure $P_1$ downstream of the filter 22 in filter chamber 40 (FIG. 2) as long as this critical pressure ratio, $P_B/P_1 \leq 0.53$, is maintained.

As particles are deposited on the filter 22, the pressure drop $\Delta P_f$ across the filter 22 increases, and the stagnation pressure $P_1$ downstream of the filter medium 22 in filter chamber 40 decreases. This decrease in the stagnation pressure $P_1$ also occurs in the bellows chamber 90 because of the direct connections of tubes 16 and 130, as described above. Such a decrease of pressure $P_1$ in bellows chamber 90 allows the bellows wall 94 to contract until the spring force of the bellows wall 94 equals the force exerted by the decreased air pressure $P_1$ on the ends of the bellows chamber 90. As the bellows 72 contracts, the bellows rod 76, slide rod 80 and slide 62 are pulled by the bellows 72, thus exposing or opening more of the slotted orifice 60. Consequently, a decrease in the stagnation pressure $P_1$ downstream of the filter medium 22 results in a simultaneous and predictable increase in the flow area of the slotted orifice 60, which in turn results in a constant volumetric flow rate Q through the sampler 10, as described by Equation 2.

Essentially, in reference to equation (2) above, a decrease of stagnation pressure $P_1$ in the numerator would result in a decrease in volumetric flow rate Q in the absence of some compensating change in another parameter. The opening of slide 62 provides that compensation by increasing the flow area $A_s$ by opening more of the orifice 60, which area $A_s$ is also in the numerator. When the orifice 60 is slotted with parallel lateral sides 132, 134, as shown in FIG. 4, the increase in effective flow area $A_s$ attributable to the orifice 60 is directly proportional to the linear movement of slide 62, which is caused by the increase in pressure drop $\Delta P_f$ across the filter 22, which when subtracted from $P_0$ equals stagnation pressure $P_1$ downstream of filter membrane 22. Consequently, the decrease in stagnation pressure $P_1$ in the numerator of formula (2) is offset by the compensating increase in effective flow area $A_s$ of the slotted orifice 60 in the flow controller 50, thereby automatically maintaining constant volumetric flow rate Q through the sampler apparatus 10.

It should be noted that, while the principal benefit and effectiveness of the flow controller 50 is in maintaining constant volumetric flow rate Q in particulate samplers wherein thin film, porous filter membranes that tend to load and begin to plug quickly are needed, its usefulness is not limited to those kinds of filter media. It also works well with the more conventional fibrous filter media where decrease in stagnation pressure $P_1$ downstream of the filter medium 22 is not as pronounced as with the non-fibrous membrane media. The only change is that the flow controller 50, and particularly the slide 62, does not have to be as active as when the changes in stagnation pressure $P_1$ are more pronounced. There are also applications where the benefits of the flow controller 50 can be particularly advantageous, even with fibrous filter media. For example, there are circumstances where total suspended particulate matter (TSP) in the air, not just the $PM_{10}$ fraction, have to be measured. In those circumstances, where all the particles collected in a sample period, such as 24 hours, are collected on a fibrous filter, there can be sufficient particulate loading on even a fibrous filter to cause significant pressure drop across the filter, thus causing a decrease in stagnation pressure $P_1$ downstream of the filter. In those circumstances, or any circumstances where there is a significant change in pressure drop $\Delta P_f$ across a filter medium, the flow controller 50 according to this invention can be useful in maintaining constant volumetric flow control through an aerosol sampler and filter.

The flow controller 50 of this invention is particularly advantageous in an aerosol sampler 150 that has alternate embodiment filter, holder, sampling module, and analyzer assembly 200, as shown in FIG. 5. In this embodiment 200, a continuous tape or strip of filter medium 202 is provided by supply reel 204 and take-up reel 206, and the filter tape 202 passes through a filter chamber 208. The air flow stream also flows through filter chamber 208. Essentially, the air stream flows from a sampler inlet (not shown in FIG. 5, but similar to the sampler inlet 12 shown in FIG. 1) and then through duct 13 into the filter chamber 208. In the filter chamber 208, the air stream is drawn through the portion of the filter medium 202 that is positioned in the filter chamber 208, and the particulate matter in the air stream is captured and retained on that portion of the filter medium 202.

This sampler 150 may also include an analyzer apparatus 210, such as a beta particle source 214, for example radioactive carbon $^{14}C$, and a beta particle preamp assembly and detector 212 positioned on opposite sides of the filter membrane 202. When there is particulate matter on the filter medium 202, some of the beta particles emitted by the source 214 will be attenuated by the particulate matter, so they will not reach the detector 212, and the detector 212 will count fewer beta particles than would be counted if the filter medium 202 was olean. Therefore, the beta particle count measured by the detector 212 is indicative of the presence of particulate matter deposited on the filter medium 202 and can be related to mass concentration $M_c$ by theory and previous calibration.

In operation, the filter medium 202 can be advanced to the point first that the portion thereof on which particles are to be deposited is positioned in the analyzer apparatus 210, so a beta count of the clean filter medium 202 can be taken for a background count. Then, the filter medium tape 202 can be advanced to position that portion in the filter chamber 208, and the sampler 150 is operated in a manner similar to that described above for the sampler embodiment 10 for a prescribed period of time. Such a time may be, for example, 24 hours. However, during that 24-hour time period, it may be desirable to determine particulate concentrations every hour or at other time intervals less than 24 hours. To accomplish this, the filter membrane tape 202 can be advanced every hour, and readings from the beta analyzer 210 can be taken and recorded every such 1-hour period.

If the filter medium 202 is a thin film, non-fibrous, porous membrane, for example, PTFE, as described above, the particulate loading thereon may cause substantial change in pressure drop $\Delta P_f$ across the filter medium 202, thus decreasing stagnation pressure $P_1$ downstream of the filter medium 202, as described above. Consequently, the stagnation pressure $P_1$ will fluctuate up and down hourly. In such circumstances, the flow controller 50 of this invention (not shown in FIG. 5, but essentially the same as shown in FIGS. 1 and 3 and as described above) can be used very advantageously in the sampler 150, because it automatically makes the required adjustment in orifice 60 flow area to maintain constant volumetric flow rate Q, as described above and by equation (2). It also has the advantage of allowing a sample to be taken for the entire sample period desired, regardless of how much the filter is loaded. Prior to this invention, the only way to keep the flow rate Q constant under conditions where fluctuating or changing pressure drop $\Delta P_f$ across the filter was a problem, was to monitor the stagnation pressure $P_1$ downstream of the filter and to abort that sampling period when the drop or change in $P_1$ exceeded a tolerable level.

While the description above refers to ambient air, ambient pressure, and ambient temperature usually in terms of atmospheric air, pressure, and temperature, this invention or the use of this invention should not be considered so restrictive. The term ambient when applied to air, pressure, or temperature for purposes of this invention can mean any air or other gas and any reference pressure or temperature that is essentially upstream of the filter in the apparatus or method of this invention. Also, while the description above referred mostly to aerosol particles, aerosol can be any gaseous suspension of liquid or solid, and this invention is equally applicable to obtaining samples of all such aerosols. The principal feature of the invention, as described above, is to provide a method and apparatus for use in circumstances where constant volumetric flow rate has to be maintained, even though the pressure drop across the filter may change significantly during a sampling period.

The foregoing is considered as illustrative only of the principles of the invention. Further, since numerous modifications and changes will readily occur to those skilled in the art, it is not desired to limit the invention to the exact construction and operation shown and described, and accordingly all suitable modifications and equivalents may be resorted to falling within the scope of the invention as defined by the claims which follow.

The embodiments of the invention in which an exclusive property or privilege is claimed are defined as follows:

1. Aerosol sampler apparatus for collecting liquid or solid matter that is borne in air, comprising:

air channeling means for channeling a said stream of flowing air through said sampler apparatus;

filter means positioned in said air channeling means for intercepting and retaining said matter that is borne in said stream of air while allowing said stream of air to pass therethrough;

flow controller means positioned in said air channeling means downstream of said filter means for maintaining said stream of air flowing at a constant volumetric flow rate, said flow controller means including a critical flow orifice having a variable flow area positioned in said air channeling means, and flow area adjusting means for adjusting the flow area through said critical flow orifice in response to changes in resistance to the flow of air through said filter means to keep the volumetric flow rate of the air flowing through said air channeling means constant; and air pump means in said air channeling means for causing said stream of air to flow through said critical flow orifice at sonic velocity to maintain sonic shock wave choked flow condition in said critical flow orifice.

2. The aerosol sampler apparatus of claim 1, wherein said filter means is positioned such that all of the air flowing through said air channeling means flows through said filter means.

3. The aerosol sampler apparatus of claim 1, wherein said flow controller means includes a partition positioned across said air channeling means, said critical flow orifice extending therethrough such that all of the air flowing through said air channeling means passes through the critical flow orifice.

4. The aerosol sampler apparatus of claim 3, wherein said flow area adjusting means includes a slide slideably positioned adjacent and partially occluding said critical flow orifice such that movement of said slide in one direction increases the flow area of said critical flow orifice and movement of said slide in the opposite direction decreases the flow area of said critical flow orifice.

5. The aerosol sampler apparatus of claim 3, wherein said critical flow orifice is in the configuration of an elongated slot with substantially parallel lateral sides, and said slide is moveable along an axis parallel to said parallel sides of said critical flow orifice, such that said variation in flow area of said critical flow orifice is proportional to linear movement of said slide.

6. The aerosol sampler apparatus of claim 5, wherein said flow area adjusting means also includes actuator means connected to said slide for imparting linear movement of said slide along said axis in relation to said critical flow orifice.

7. The aerosol sampler apparatus of claim 6, wherein said actuator means includes a pressure-sensitive driver means for generating linear movement of said slide in response to variations in air pressure drop across said filter means.

8. The aerosol sampler apparatus of claim 7, wherein said driver means includes an axially expandable and contractible bellows connected to said slide for imparting linear movement to said slide, said bellows having an interior chamber that is in air flow communication with said air channeling means between said filter means and said partition such that said interior chamber of said bellows is maintained at about the same pressure as the air pressure in said air channeling means downstream of said filter means, and wherein said bellows expands and contracts in response to changes in pressure in said interior chamber of said bellows.

9. The aerosol sampler apparatus of claim 8, including a stagnation chamber in said air channeling means between said filter means and said flow controller that is sufficiently large to have essentially stagnation pressure therein, and wherein said interior chamber of said bellows is in air flow communication with said stagnation chamber such that the pressure in said interior chamber of said bellows essentially corresponds to the stagnation pressure downstream of said filter means.

10. The aerosol sampler apparatus of claim 9, wherein said bellows has a spring constant such that its linear expansion and contraction occurs in direct, linear proportion to changes in pressure in the interior chamber of said bellows.

11. The aerosol sampler apparatus of claim 3, wherein said partition also has a bypass critical flow orifice therethrough, and wherein said air pump also has sufficient capacity and power to maintain critical or choked flow conditions of the air flowing through both said adjustable critical flow orifice and said bypass orifice.

12. The aerosol sampler apparatus of claim 1, wherein said filter means includes a non-fibrous filter membrane positioned across said air channeling means.

13. The aerosol sampler apparatus of claim 12, wherein said filter membrane is comprised of a porous, thin film polytetrafluoroethylene (PTFE).

14. A method of maintaining constant volumetric flow rate of air through an aerosol sampler that has an air channel for conducting a stream of air collected from ambient air at ambient pressure $P_0$ through a filter to capture aerosol particulate matter from the stream of air, comprising the steps of:

positioning a partition with an orifice having a variable cross-sectional or flow area therethrough across said air channel downstream from said filter;

pulling air through said air channel at a sufficient capacity to cause a pressure drop through said orifice such that a back pressure $P_B$ is created downstream of said orifice and maintaining said back pressure $P_B$ low enough such that the ratio of the back pressure $P_B$ to the stagnation pressure $P_1$ downstream of said filter and upstream of said orifice does not exceed 0.53, ($P_B/P_1 \leq 0.53$), to create and maintain critical or choked flow condition in said orifice; and increasing the effective cross-sectional or flow area of said orifice in response to increases in the amount of pressure drop across the filter medium.

15. The method of claim 14, including the step of increasing the effective cross-sectional or flow area of the orifice in direct, linear proportion to increases in the amount of pressure drop across the filter medium.

16. The method of claim 14, including the step of monitoring the stagnation pressure $P_1$ in the air channel downstream of the filter medium and increasing or decreasing the effective cross-sectional or flow area of said orifice in inverse proportion to increases and decreases in the stagnation pressure $P_1$.

17. The method of claim 16, including the steps of positioning a moveable slide adjacent said orifice for adjustably occluding portions of the orifice to change its effective flow area, connecting an expandable and contractible bellows to said slide for moving the slide in relation to the orifice, applying said stagnation pressure $P_1$ to said bellows in such a manner as to cause contraction of said bellows as the stagnation pressure decreases and thereby increasing the effective flow area of the orifice.

18. The method of claim 17, including the step of shaping said orifice as an elongated slotted aperture through said partition with two opposite elongated sides of said aperture being parallel to each other, positioning said slide adjacent said aperture to be moveable along an axis that is substantially parallel to said sides such that movement of said slide causes variations in said effective flow area of said orifice in proportion to the distance the slide moves.

19. The method of claim 18, including the step of providing said bellows with a spring constant such that decreases in said stagnation pressure cause linearly proportional increases in said effective flow area of said orifice.

20. A method of collecting particle samples from ambient air, comprising the steps of:

drawing a sample of ambient air through an inlet and through a non-fibrous, thin film, porous membrane for capturing and retaining aerosol matter on aid membrane; and maintaining constant volumetric flow rate of the air through the inlet and filter membrane by pulling the air through a critical flow orifice having a variable flow area, maintaining back pressure $P_B$ immediately downstream of the orifice low enough to maintain critical or choked flow condition in the orifice, and increasing the effective flow area of the orifice in direct, linear proportion to increases in the amount of pressure drop across the filter membrane.

21. The method of claim 20, including the step of drawing said air sample through a filter membrane that is comprised of polytetrafluoroethylene (PTFE).

22. The method of claim 21 including the step of drawing said air sample through a filter membrane that has pores ranging in size from about 0.1 to 5.0 micrometers.

23. The method of claim 20, including the step of drawing said air sample through a filter membrane that comprises submicrometer fibers.

24. The method of claim 20, including the steps of drawing said air sample through a filter membrane that is substantially non-fibrous and very retentive of aerosol matter and measuring aerosol matter retained on said membrane by measuring beta particle flux transmitted therethrough.

25. Aerosol sampler apparatus, comprising:

air channeling means for channeling a stream of flowing air through said sampler apparatus;

filter means positioned in said air channeling means for intercepting and retaining particle that are borne in said stream of flowing air while allowing said stream of flowing air to pass therethrough;

flow controller means positioned in said air channeling means downstream of said filter means for maintaining said stream of air flowing at a constant volumetric flow rate, said flow controller means including a partition positioned across said air channeling means with an orifice in the configuration of an elongated slot having substantially parallel lateral sides extending through said partition, a slide positioned adjacent and partially occluding said orifice, said slide being moveable along an axis parallel to said parallel lateral sides of said orifice; and air pump means in said air channeling means for causing said stream of air to flow through said orifice at sonic velocity.

26. The aerosol sampler of claim 25, including actuator means connected to said slide for imparting linear movement of said slide along said axis in relation to said orifice.

27. The aerosol sampler apparatus of claim 26, wherein said actuator means includes a pressure-sensitive driver means for generating linear movement of said slide in response to variations in pressure drop across said filter means.

28. The aerosol sampler apparatus of claim 27, wherein said driver means includes an axially expandable and contractible bellows connected to said slide for imparting linear movement to said slide, said bellows having an interior chamber that is in air flow communication with said air channeling means between said filter means and said partition such that said interior chamber of said bellows is maintained at about the same pressure as the air pressure in said air channeling means downstream of said filter means, and wherein said bellows expands and contracts in response to changes in pressure in said interior chamber of said bellows.

29. The aerosol sampler apparatus of claim 28, including a stagnation chamber in said air channeling means between said filter means and said flow controller that is sufficiently large to have essentially stagnation pressure therein, and wherein said interior chamber of said bellows is in air flow communication with said stagnation chamber such that the pressure in said interior chamber of said bellows essentially corresponds to the stagnation pressure downstream of said filter means.

30. The aerosol sampler apparatus of claim 29, wherein said bellows has a spring constant such that its linear expansion and contraction occurs in direct, linear proportion to changes in pressure in the interior chamber of said bellows.

31. The aerosol sampler apparatus of claim 25, wherein said partition also has a bypass critical flow orifice therethrough, and wherein said air pump also has sufficient capacity and power to maintain critical or choked flow conditions of the air flowing through both said adjustable critical flow orifice and said bypass orifice.

32. The aerosol sampler apparatus of claim 25, wherein said filter means includes a non-fibrous filter membrane positioned across said air channeling means.

33. The aerosol sampler apparatus of claim 32, wherein said filter membrane is comprised of a porous, thin film polytetrafluoroethylene (PTFE).

34. Aerosol sampler apparatus, comprising:

air channeling means for channeling a stream of flowing air through said sampler apparatus;

filter means positioned in said air channeling means for capturing and retaining particles from the air stream flowing therethrough;

flow controller means positioned in said air channeling means for maintaining said stream of air flowing at a constant volumetric flow rate through said filter means, said flow controller means including a partition positioned across said air channeling means with an orifice extending through said partition, a gate slidably positioned adjacent and partially occluding said orifice, a bellows that has an axially expandable and contractible wall connected to said gate and enclosing an interior bellows chamber, said wall being expandable and contractible in response to changes in pressure in said interior bellows chamber, and said interior bellows chamber being connected in common pressure relation to said air channeling means between said filter means and said orifice such that decreases in pressure between said filter means and said orifice cause movement of said gate to occlude less of said orifice and increases in pressure between said filter means and said orifice cause movement of said gate to occlude more of said orifice; and air pump means in said air channeling means for causing said stream of air to flow through said orifice at sonic velocity.

35. The improvement of claim 34, wherein said bellows has a spring constant such that it expands and contracts in direct proportion to changes in said stagnation pressure.

36. The improvement of claim 35, wherein said orifice is in the shape of a narrow, elongated slot with elongated, parallel lateral sides, and wherein said slide is moveable along an axis parallel to said lateral sides such that variation of said flow area of said orifice is in linear, direct proportion to linear movement of said slide and to changes in said stagnation pressure.

37. Aerosol sampler apparatus, comprising:

air channeling means for channeling a stream of flowing air through said sampler apparatus;

filter means positioned in said air channeling means for capturing particles from the air stream flowing through the air channeling means and filter means;

a partition positioned in said air channeling means downstream from said filter means with an orifice extending through said partition;

closure means adjacent said orifice for adjustably occluding portions of said orifice to vary the effective cross-sectional area of said orifice;

actuator means connected to said closure means and responsive to pressure between said filter means and said orifice for moving said closure means to decrease occlusion of said orifice when pressure between said filter means and said orifice decreases; and air pump means in said air channeling means for causing said stream of air to flow through said orifice at sonic velocity.

38. The aerosol sampler apparatus of claim 37, wherein said orifice has a first side that is substantially straight and a second side that is substantially straight.

39. The aerosol sampler apparatus of claim 38, wherein said closure means includes a gate positioned adjacent said orifice in such a manner that said gate spans the orifice from said first side to said second side, said gate being moveable in relation to said orifice in such a manner as to adjustably occlude more or less of said orifice while spanning said orifice between said first side and said second side to adjustably decrease or increase, respectively, said effective cross-sectional area of said orifice.

40. The aerosol sampler apparatus of claim 39, wherein said orifice is elongated in shape, thereby defining a longitudinal axis extending in the elongated direction of orifice, and wherein said gate is moveable in a manner that occludes more or less of the orifice in generally the direction of the longitudinal axis of the orifice.

41. The aerosol sampler apparatus of claim 39, wherein said first side and said second side are substantially parallel to each other.

42. The aerosol sampler apparatus of claim 39, wherein said partition also has a bypass orifice extending through said partition, and wherein said air pump means causes said stream of air to flow through said orifice and said bypass orifice at sonic velocity.

43. The aerosol sampler apparatus of claim 39, wherein said actuator means includes pressure-sensitive transducer means connected in pressure sensing relation to said air channeling means between said filter and said orifice and connected mechanically to said gate for moving said gate in a direction to occlude less of said orifice in response to pressure decrease in said air channeling means between said filter means and said orifice.

44. The aerosol sampler apparatus of claim 43, wherein said pressure-sensitive transducer means produces mechanical movement in magnitude directly proportional to changes in pressure in said air channeling means between said filter means and said orifice.

45. The aerosol sampler apparatus of claim 44, wherein said pressure-sensitive transducer includes a bellows with an expandable and contractible wall that encloses an interior chamber, said interior chamber being connected in common pressure communication with said air channeling means between said filter means and said orifice, said wall being expandable and contractible in relation to pressure in said interior chamber.

46. The aerosol sampler apparatus of claim 45, wherein said wall is expandable and contractible in a linear direction in constant direct proportional relation to pressure in said interior chamber, and wherein said wall is connected to said gate.

* * * * *

UNITED STATES PATENT AND TRADEMARK OFFICE
CERTIFICATE OF CORRECTION

PATENT NO. : 5,317,930
DATED : June 7, 1994
INVENTOR(S) : James B. Wedding

It is certified that error appears in the above-indentified patent and that said Letters Patent is hereby corrected as shown below:

In the Abstract:

Line 12, change "this" to --thin--.

In Background of the Invention:

In column 2, line 17, change "an" to --and--.

In column 2, line 59, after "criteria." delete --.--.

In Summary of the Invention:

In column 2, line 63, after "an" delete --aerosol--.

In Detailed Description of the Preferred Embodiments:

In column 5, line 4, change "aerosol" to --air borne--.

In column 5, line 57, change "1" to --12--.

In column 6, line 51, change "1" to --12--.

UNITED STATES PATENT AND TRADEMARK OFFICE
CERTIFICATE OF CORRECTION

PATENT NO. : 5,317,930
DATED : June 7, 1994
INVENTOR(S) : James B. Wedding

It is certified that error appears in the above-indentified patent and that said Letters Patent is hereby corrected as shown below:

In column 8, line 19, change second instance of "a" to --an--.

In column 8, line 34, after "also" insert --be--.

In column 11, line 44, change "olean" to --clean--.

In column 12, line 54, after "a" delete --said--.

In column 12, line 55, change "flowing air" to --air flowing--.

In column 13, line 57, after "controller" insert --means--.

In column 14, line 3, after "pump" insert --means--.

In column 14, line 5, after "the" insert --stream of--.

In column 14, line 6, delete --adjustable--.

In column 14, line 6, after "orifice" insert --having a variable flow area--.

In column 14, line 38, after "filter" delete --medium--.

UNITED STATES PATENT AND TRADEMARK OFFICE
CERTIFICATE OF CORRECTION

PATENT NO. : 5,317,930
DATED : June 7, 1994
INVENTOR(S) : James B. Wedding

It is certified that error appears in the above-identified patent and that said Letters Patent is hereby corrected as shown below:

In column 14, line 41, after "filter" delete --medium--.

In column 15, line 5, change "aid" to --said--.

In column 15, line 37, change "particle" to --particles--.

In column 16, line 27, after the first instance of "said" delete --adjustable critical flow--.

In column 16, line 27, after "bypass" insert --critical flow--.

In column 18, line 4, after "of" insert --said--.

Signed and Sealed this

Twelfth Day of September, 1995

Attest:

BRUCE LEHMAN

Attesting Officer

Commissioner of Patents and Trademarks